United States Patent
Sekine et al.

(10) Patent No.: US 8,039,611 B2
(45) Date of Patent: Oct. 18, 2011

(54) 2'-HYDROXYL GROUP-MODIFIED RIBONUCLEOSIDE DERIVATIVES

(75) Inventors: Mitsuo Sekine, Yokohama (JP); Takeshi Yamada, Yokohama (JP); Hisao Saneyoshi, Yokohama (JP); Kohji Seio, Yokohama (JP)

(73) Assignee: Tokyo Institute of Technology, Tokyo (JP)

( * ) Notice: Subject to any disclaimer, the term of this patent is extended or adjusted under 35 U.S.C. 154(b) by 413 days.

(21) Appl. No.: 12/224,677

(22) PCT Filed: Mar. 8, 2007

(86) PCT No.: PCT/JP2007/054533
§ 371 (c)(1),
(2), (4) Date: Dec. 17, 2008

(87) PCT Pub. No.: WO2007/102581
PCT Pub. Date: Sep. 13, 2007

(65) Prior Publication Data
US 2010/0016574 A1    Jan. 21, 2010

(30) Foreign Application Priority Data
Mar. 8, 2006    (JP) .................................. 2006-063358

(51) Int. Cl.
*C07H 21/00*    (2006.01)
(52) U.S. Cl. ............. 536/25.3; 536/22.1; 536/23.1; 536/25.31; 536/25.5
(58) Field of Classification Search ............ None
See application file for complete search history.

(56) References Cited

U.S. PATENT DOCUMENTS

| | | |
|---|---|---|
| 5,719,271 A | 2/1998 | Cook et al. |
| 6,147,200 A | 11/2000 | Manoharan et al. |
| 6,403,779 B1 | 6/2002 | Kawasaki et al. |
| 2004/0048826 A1 | 3/2004 | Cook et al. |

FOREIGN PATENT DOCUMENTS

| | | |
|---|---|---|
| JP | 5-504552 A | 7/1993 |
| JP | 2003-520200 A | 7/2003 |
| WO | WO-01/14400 A1 | 3/2001 |

OTHER PUBLICATIONS

Bazin et al., "Hydrolysis of Cyanoethylated Carbohydrates: Synthesis of New Carboxylic Derivatives of Sucrose, D-Glucose and D-Fructose," J. Carbohydrate Chemistry, vol. 14, No. 8, 1995, pp. 1187-1207.
Prakash et al., "2'-O-[2-(Amino)-2-oxoethyl] Oligonucleotides," Organic Letters, vol. 5, No. 4, 2003, pp. 403-406.
Kachalova et al., "Synthesis of Modified Nucleotide Building Blocks Containing Electrophilic Groups in the 2'-Position," Nucleosides, Nucleotides & Nucleic Acids, vol. 19, No. 10-12, 2000, pp. 1693-1707.
Keller et al., "Synthesis and hybridization properties of oligonucleotides containing 2'-O-modified ribonucleotides," Nucleic Acids Research, vol. 21, No. 19, 1993, pp. 4499-4505.
Keller et al., "51. A General Method for the Synthesis of 2'-O-Modified Ribonucleosides," Helvetica Chimica Acta, vol. 76, 1993, pp. 884-892.

*Primary Examiner* — Patrick Lewis
(74) *Attorney, Agent, or Firm* — Birch, Stewart, Kolasch & Birch, LLP

(57) ABSTRACT

Provided is a ribonucleoside derivative represented by General Formula (I):

[Formula 1]

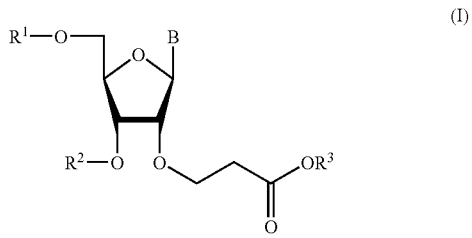

(wherein $R^1$ represents a hydrogen atom or the like, $R^2$ represents a hydrogen atom or the like, $R^3$ represents a methyl group or the like, and B represents a nucleic acid base residue optionally having a protecting group or a modifying group). An RNA containing this ribonucleoside derivative shows excellent hybridization ability and resistance to nuclease.

12 Claims, No Drawings

2'-HYDROXYL GROUP-MODIFIED RIBONUCLEOSIDE DERIVATIVES

TECHNICAL FIELD

The present invention relates to a novel ribonucleoside derivative having a 2'-hydroxyl group modified with, for example, an alkoxycarbonylethyl group, and a nucleic acid derivative containing the ribonucleoside derivative. The alkoxycarbonylethyl group can be converted to, for example, a hydroxyethyl group or a carbamoylethyl group by a chemical reaction. RNAs containing ribonucleosides having these modifying groups are expected to have properties such as excellent hybridization ability and nuclease resistance and are expected to be useful as nucleic acid detection probes or artificial RNAs for an antisense method, an RNAi method, and the like.

BACKGROUND ART

Synthesis of an RNA having a modified 2'-hydroxyl group requires a ribonucleoside monomer intermediate having a modified 2'-hydroxyl group. Main conventional methods of synthesizing this monomer intermediate are two: One is a method wherein the 2'- or 3'-hydroxyl group of a ribonucleoside of which the base site and the 5'-hydroxyl group are protected is converted to alkoxide with NaH, and then the ribonucleoside is subjected to a reaction with alkyl halide (Non-Patent Document 1). In this method, since in addition to a 2'-modified product a 3'-modified product, which is a positional isomer, is produced in a large amount, many cases have difficulties in separating them. In the other method, a ribonucleoside derivative of which the base site and the 3'- and 5'-hydroxyl groups are protected is reacted with NaH to alkylate the hydroxyl group at the 2'-position to form alkoxide, or is reacted with alkyl halide in the presence of a strong organic base such as BEMP (Non-Patent Document 2). In this method, a protecting group that can simultaneously protect both 3'- and 5'-hydroxyl groups is necessary, and, in general, a 1,1,3,3-tetraisopropyldisiloxane-1,3-diyl (TIPS) group or a di(tert-butyl)silanyl (DBS) group is used. However, these protecting groups are unstable to reagents such as NaH and BEMP and thereby have a major problem that by-products are produced. Since the basic conditions employed in both synthesis methods described above are strict, it is generally impossible to incorporate a functional group such as methyl ester or ethyl ester into an alkyl halide derivative that is used as a modifying group-inducing reagent. Consequently, in order to maintain the stability, only a group having large steric hindrance, such as tert-butyl ester, can be incorporated as an ester skeleton.

[Non-Patent Document 1] Richard H. Griffey, Brett P. Monia, Lendall L. Cummins, Susan Freier, Michael J. Greig, Charles J. Guinosso, Elena Lesnik, Sherilynn M. Manalili, Venkatraman Mohan, Steven Owens, Bruce R. Ross, Henri Sasmor, Ed Wancewicz, Kurt Weiler, Patrick D. Wheeler, and P. Dan Cook, J. Med. Chem. 1996, 39, 5100-5109.

[Non-Patent Document 2] Grotli, M., Douglas, M., Beijer, B., Garcia, R. G., Eritja, R., and Sproat, B., J. Chem. Soc., Perkin Trans. 1, 1997, 2779-2788.

DISCLOSURE OF INVENTION

Problems to be Solved by the Invention

As described above, in the conventional methods, the ester skeleton that can be incorporated into the 2'-hydroxyl group of a ribonucleoside is limited to specific one such as tert-butyl ester. The present invention has been accomplished under such technical background, and it is an object to provide means for incorporating a simpler ester skeleton into the 2'-hydroxyl group of ribonucleoside.

Means for Solving the Problem

The present inventors have conducted intensive studies in order to solve the above-mentioned problems and, as a result, have found the fact that an alkoxycarbonylethyl group can be incorporated into the 2'-hydroxyl group of a ribonucleoside derivative by a Michael reaction using an acrylic acid ester, which is α,β-unsaturated ester, under very mild reaction conditions. The present invention has been completed based on this finding.

Accordingly, the present invention provides the following (1) to (12):

(1) A ribonucleoside derivative represented by General Formula (I):

[Formula 16]

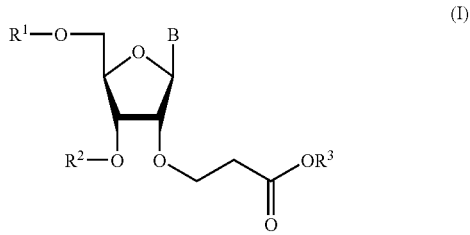

(wherein $R^1$ represents a hydrogen atom or a protecting group for a hydroxyl group; $R^2$ represents a hydrogen atom, a protecting group for a hydroxyl group, or a group expressed by General Formula (III):

[Formula 17]

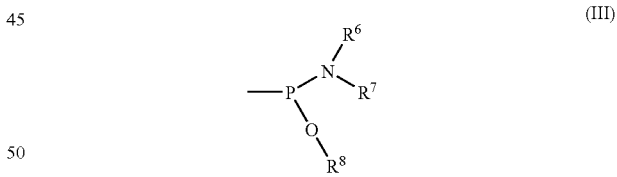

(wherein $R^6$ and $R^7$ are the same or different and each represents an alkyl group, or binds to each other to form a ring that optionally contains a hetero atom; and $R^8$ represents a protecting group for a phosphate group); $R^3$ represents a hydrogen atom, an alkyl group optionally having a substituent, an aralkyl group optionally having a substituent, an alkenyl group optionally having a substituent, an alkynyl group optionally having a substituent, or an aryl group optionally having a substituent; and B represents a nucleic acid base residue optionally having a protecting group or a modifying group);

(2) The ribonucleoside derivative according to (1) wherein $R^3$ in General Formula (I) represents a methyl group or a 2,2,2-trifluoroethyl group;

(3) A ribonucleoside derivative represented by General Formula (II):

[Formula 18]

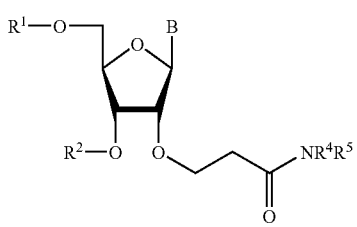

(II)

(wherein $R^1$ represents a hydrogen atom or a protecting group for a hydroxyl group; $R^2$ represents a hydrogen atom, a protecting group for a hydroxyl group, or a group expressed by General Formula (III):

[Formula 19]

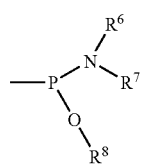

(III)

(wherein $R^6$ and $R^7$ are the same or different and each represents an alkyl group, or binds to each other to form a ring that optionally contains a hetero atom; and $R^6$ represents a protecting group for a phosphate group); $R^4$ and $R^5$ are the same or different and each represents a hydrogen atom, an alkyl group optionally having a substituent, an aralkyl group optionally having a substituent, an alkenyl group optionally having a substituent, an alkynyl group optionally having a substituent, or an aryl group optionally having a substituent; and B represents a nucleic acid base residue optionally having a protecting group or a modifying group);

(4) The ribonucleoside derivative according to (3) wherein $R^4$ and $R^5$ in General Formula (II) each represent a methyl group;

(5) The ribonucleoside derivative according to (3) wherein at least one of $R^4$ and $R^5$ in General Formula (II) represents a hydrogen atom;

(6) A process for producing a ribonucleoside derivative comprising:

reacting a ribonucleoside derivative represented by General Formula (IV):

[Formula 20]

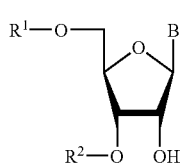

(IV)

(wherein $R^1$ represents a hydrogen atom or a protecting group for a hydroxyl group; $R^2$ represents a hydrogen atom, a protecting group for a hydroxyl group, or a group expressed by General Formula (III):

[Formula 21]

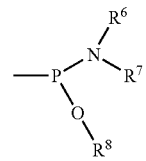

(III)

(wherein $R^6$ and $R^7$ are the same or different and each represents an alkyl group, or binds to each other to form a ring that optionally contains a hetero atom; and $R^8$ represents a protecting group for a phosphate group); and B represents a nucleic acid base residue optionally having a protecting group or a modifying group) with an acrylic acid ester represented by General Formula (V):

[Formula 22]

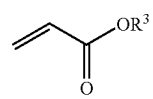

(V)

(wherein $R^3$ represents a hydrogen atom, an alkyl group optionally having a substituent, an aralkyl group optionally having a substituent, an alkenyl group optionally having a substituent, an alkynyl group optionally having a substituent, or an aryl group optionally having a substituent) to obtain a ribonucleoside derivative represented by General Formula (I):

[Formula 23]

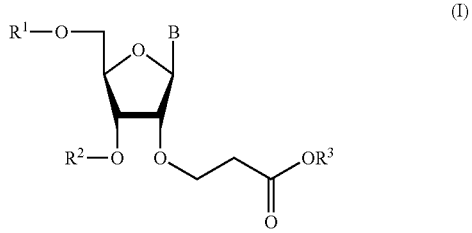

(I)

(wherein $R^1$, $R^2$, $R^3$, and B have the same meanings as mentioned above);

(7) The process for producing a ribonucleoside derivative according to (6) wherein $R^3$ in General Formula (I) represents a methyl group or a 2,2,2-trifluoroethyl group;

(8) A nucleic acid derivative represented by General Formula (VI):

[Formula 24]

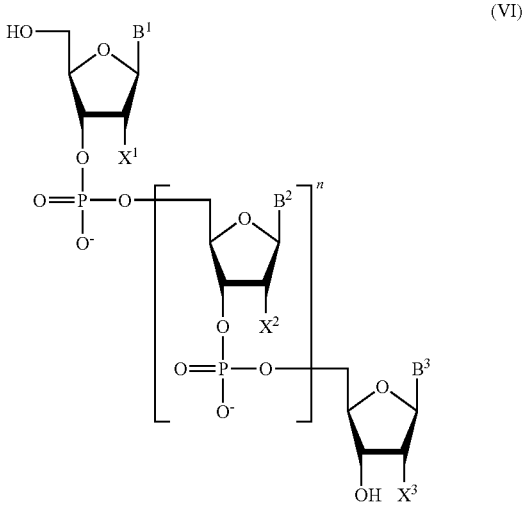

(wherein $B^1$, $B^2$, and $B^3$ are the same or different and each represents a nucleic acid base residue optionally having a protecting group or a modifying group; repeated n $B^2$s may be different; $X^1$, $X^2$, and $X^3$ are the same or different and each represents a hydrogen atom, a hydroxyl group, a methoxy group, a cyanoethoxy group, a group expressed by General Formula (VII):

[Formula 25]

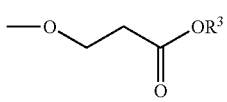

(wherein $R^3$ represents a hydrogen atom, an alkyl group optionally having a substituent, an aralkyl group optionally having a substituent, an alkenyl group optionally having a substituent, an alkynyl group optionally having a substituent, or an aryl group optionally having a substituent), or a group expressed by General Formula (VIII):

[Formula 26]

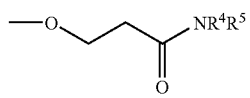

(wherein $R^4$ and $R^5$ are the same or different and each represents a hydrogen atom, an alkyl group optionally having a substituent, an aralkyl group optionally having a substituent, an alkenyl group optionally having a substituent, an alkynyl group optionally having a substituent, or an aryl group optionally having a substituent); repeated n $X^2$s may be different; n is an integer of 1 or more; and at least one of $X^1$, $X^2$, and $X^3$ represents a group expressed by General Formula (VII) or (VIII));

(9) The nucleic acid derivative according to (8) wherein $R^3$ in General Formula (VII) represents a methyl group or a 2,2,2-trifluoroethyl group;

(10) The nucleic acid derivative according to (8) wherein $R^4$ and $R^5$ in General Formula (VIII) represent a methyl group;

(11) The nucleic acid derivative according to (8) wherein at least one of $R^4$ and $R^5$ in General Formula (VIII) represents a hydrogen atom; and

(12) A process for preparing a ribonucleoside derivative or a nucleic acid derivative containing the ribonucleoside derivative as a constituent, the process comprising:

treating a ribonucleoside derivative represented by General Formula (I):

[Formula 27]

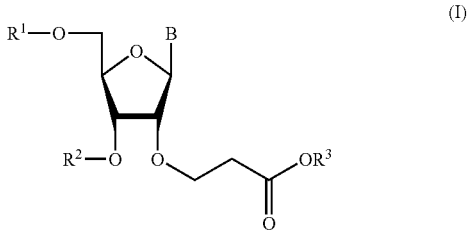

(wherein $R^1$ represents a hydrogen atom or a protecting group for a hydroxyl group; $R^2$ represents a hydrogen atom, a protecting group for a hydroxyl group, or a group expressed by General Formula (III):

[Formula 28]

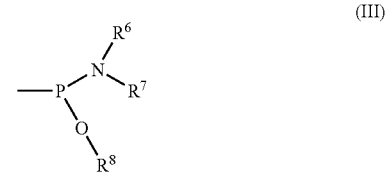

(wherein $R^6$ and $R^7$ are the same or different and each represents an alkyl group, or binds to each other to form a ring that optionally contains a hetero atom; and $R^8$ represents a protecting group for a phosphate group); $R^3$ represents a hydrogen atom, an alkyl group optionally having a substituent, an aralkyl group optionally having a substituent, an alkenyl group optionally having a substituent, an alkynyl group optionally having a substituent, or an aryl group optionally having a substituent; and B represents a nucleic acid base residue optionally having a protecting group or a modifying group), or a ribonucleoside derivative represented by General Formula (II):

[Formula 29]

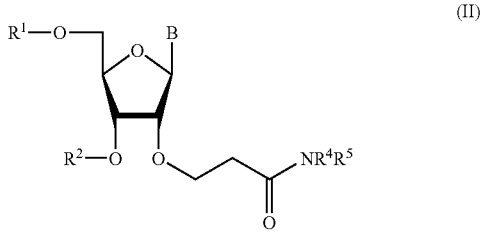

(II)

(wherein $R^1$, $R^2$, and B have the same meanings as mentioned above; and $R^4$ and $R^5$ are the same or different and each represents an alkyl group optionally having a substituent, an aralkyl group optionally having a substituent, an alkenyl group optionally having a substituent, an alkynyl group optionally having a substituent, or an aryl group optionally having a substituent), or a nucleic acid derivative containing such a ribonucleoside derivative as a constituent with a reagent containing a fluoride ion to obtain the corresponding ribonucleoside derivative represented by General Formula (IV):

[Formula 30]

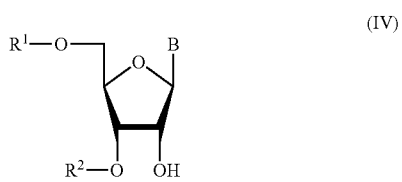

(IV)

(wherein $R^1$, $R^2$, and B have the same meanings as mentioned above), or a nucleic acid derivative containing the ribonucleoside derivative as a constituent.

Advantageous Effect of the Invention

Accordingly, the present invention enables to incorporate an ester functional group into a 2'-hydroxyl group. Therefore, various substituents will be available as modifying groups by utilizing the reactivity of this functional group, which enables to provide new materials for the antisense method and the RNAi method. In addition, since an amide group can be incorporated into a modifying group and incorporation of the functional group labeled with a fluorescent dye or a spin label is possible by utilizing the stability of this functional group, use as a probe molecule can be expected. An N-methylcarbamoylethyl group can be incorporated into a 2'-hydroxyl group by reacting, for example, methylamine to ester. This can be used as a protecting group for a 2'-hydroxyl group of novel RNA synthesis. Furthermore, development of an RNA synthesis method utilizing this protecting group can be expected.

BEST MODES FOR CARRYING OUT THE INVENTION

The present invention will now be described in detail.
The ribonucleoside derivative of the present invention is represented by General Formula (I) or (II).
$R^1$ in General Formula (I) or (II) represents a hydrogen atom or a protecting group for a hydroxyl group. The protecting group for a hydroxyl group may be a protecting group that is commonly used for the nucleoside 5'-hydroxyl group and may be a group that protects only the 5'-hydroxyl group or a group that simultaneously protects both the 3'-hydroxyl group and the 5'-hydroxyl group. Examples of the group that protects only the 5'-hydroxyl group include a trialkylsilyl group such as a tert-butyldimethylsilyl (TBDMS) group and a tert-butyldiphenylsilyl group, a benzoyl group, a substituted benzoyl group (for example, a 2-methylbenzoyl group and a 2-tert-butylbenzoyl group), and a naphthoyl group. Examples of the group that simultaneously protects both the 3'-hydroxyl group and the 5'-hydroxyl group include a TIPS group and a DBS group. When $R^2$ is a group expressed by General Formula (III), preferred protecting groups for a hydroxyl group are, for example, a 4,4'-dimethoxytrityl (DMTr) group, a 4-methoxytrityl (MMTr) group, and a pixyl group.

$R^2$ in General Formula (I) or (II) represents a hydrogen atom, a protecting group for a hydroxyl group, or a group expressed by General Formula (III). The protecting group for a hydroxyl group may be a protecting group that is commonly used for the nucleoside 3'-hydroxyl group, and examples thereof include a trialkylsilyl group such as a tert-butyldimethylsilyl (TBDMS) group and a tert-butyldiphenylsilyl group, a benzoyl group, a substituted benzoyl group (for example, a 2-methylbenzoyl group and a 2-tert-butylbenzoyl group), a naphthoyl group, a TIPS group, and a DBS group.

$R^3$ in General Formula (I) represents a hydrogen atom, an alkyl group optionally having a substituent, an aralkyl group optionally having a substituent, an alkenyl group optionally having a substituent, an alkynyl group optionally having a substituent, or an aryl group optionally having a substituent; preferably represents an alkyl group optionally having a substituent; more preferably represents a methyl group or a 2,2,2-trifluoroethyl group. In this description, the "alkyl group" is, for example, a methyl group, an ethyl group, a propyl group, an isopropyl group, a butyl group, an isobutyl group, a sec-butyl group, or a tert-butyl group. The "aralkyl group" is, for example, a benzyl group. The "alkenyl group" is, for example, an allyl group or a homoallyl group. The "alkynyl group" is, for example, a propargyl group. The "aryl group" is, for example, a phenyl group or a naphthyl group. The "alkyl group having a substituent" is, for example, a 2,2,2-trifluoroethyl group, a cyanomethyl group, or a 2,2,2-trichloroethyl group. The "aralkyl group having a substituent" is, for example, a 4-chlorobenzyl group or a 4-nitrobenzyl group. The "alkenyl group having a substituent" is, for example, a dichloroallyl group. The "aryl group having a substituent" is, for example, a 4-nitrophenyl group.

$R^4$ and $R^5$ in General Formula (II) are the same or different and each represents a hydrogen atom, an alkyl group optionally having a substituent, an aralkyl group optionally having a substituent, an alkenyl group optionally having a substituent, an alkynyl group optionally having a substituent, or an aryl group optionally having a substituent; preferably represents a hydrogen atom or an alkyl group optionally having a substituent; and more preferably represents a hydrogen atom or a methyl group. The "alkyl group" or the like has the same meaning as mentioned above.

As described below, the elimination mechanism of 2'-modifying group (carbamoylethyl moiety) of General Formula (II) varies depending on the groups of $R^4$ and $R^5$. That is, when neither $R^4$ nor $R^5$ is a hydrogen atom, the carbamoylethyl moiety is eliminated by treatment with tetrabutylammonium fluoride ($Bu_4NF$), but when at least one of $R^4$ and $R^5$ is a hydrogen atom, the carbamoylethyl moiety is stable to $Bu_4NF$. Accordingly, it is preferable that both $R^4$ and $R^5$ be other than a hydrogen atom when the carbamoylethyl moiety is used as a protecting group for a 2'-hydroxyl group and that at least one of $R^4$ and $R^5$ be a hydrogen atom when the carbamoylethyl moiety is used as a modifying group for binding, for example, a labeling agent.

B in General Formula (I) or (II) represents a nucleic acid base residue optionally having a protecting group or a modifying group. Examples of the nucleic acid base include adenine, cytosine, guanine, uracil, and thymine. Regarding the protecting group or the modifying group, in the adenine base, the amino group at the N6 position may be protected by one or two acyl groups, or an amidine protecting group may be employed. In the guanine base, the amino group at the N2 position may be protected by one or two acyl groups, or an amidine protecting group may be employed. In addition, the O6 position of the guanine base may be protected by an alkyl group such as a cyanoethyl group or an acyl group such as a diphenylcarbamoyl group. In the uracil base and the thymine base, the N3 position may be protected by an alkyl group or an acyl group. Furthermore, a pyrimidine base may have an alkyl group, an alkenyl group, an alkynyl group, an aryl group, or such a group containing a substituent such as a fluorescent functional group, a biotinyl group, an amino group, or a spin label at the 5-position.

$R^6$ and $R^7$ in General Formula (III) are the same or different and each represents an alkyl group, or binds to each other to form a ring that optionally contains a hetero atom. Examples of the alkyl group include a methyl group, an ethyl group, a propyl group, an isopropyl group, a butyl group, an isobutyl group, a sec-butyl group, and a tert-butyl group. Among them, the isopropyl group is preferred.

$R^8$ in General Formula (III) represents a protecting group for a phosphate group. Examples of the protecting group for a phosphate group include a 2-cyanoethyl group, a 4-nitrophenylethyl group, an N-(trifluoroacetyl)-4-aminobutyl group, and an N-methyl-N-(trifluoroacetyl)-4-aminobutyl group. Among them, the 2-cyanoethyl group is preferred.

Specific examples of the compound represented by General Formula (I) include 2'-O-(2-methoxycarbonylethyl)adenosine, 2'-O-(2-methoxycarbonylethyl)cytidine, 2'-O-(2-methoxycarbonylethyl)guanosine, and 2'-O-(2-methoxycarbonylethyl)uridine.

Specific examples of the compound represented by General Formula (II) include 2'-O—(N-methylaminocarbonylethyl)adenosine, 2'-O—(N-methylaminocarbonylethyl)cytidine, 2'-O—(N-methylaminocarbonylethyl)guanosine, 2'-O—(N-methylaminocarbonylethyl)uridine, 2'-O—(N,N-dimethylaminocarbonylethyl)adenosine, 2'-O—(N,N-dimethylaminocarbonylethyl)cytidine, 2'-O—(N,N-dimethylaminocarbonylethyl)guanosine, and 2'-O—(N,N-dimethylaminocarbonylethyl)uridine.

The ribonucleoside derivative represented by General Formula (I) can be produced by reacting a ribonucleoside derivative represented by General Formula (IV) with an acrylic acid ester represented by General Formula (V).

$R^3$ in General Formula (V) is the same as that described above.

The reaction is carried out under the presence of an appropriate catalyst. Examples of the catalyst include $CS_2CO_3$, $K_2CO_3$, $Na_2CO_3$, and DBU.

In addition, the reaction is carried out in a solvent that does not inhibit the reaction. An example of such a solvent is tert-butanol.

The reaction temperature is not particularly limited, but is preferably within the range of 0 to 100° C.

The reaction time is not particularly limited, but is preferably 1 to 50 hours.

The amount ratio of the ribonucleoside derivative and the acrylic acid ester used in the reaction is not particularly limited, but the reaction is preferably carried out at a molar ratio of the ribonucleoside derivative to the acrylic acid ester within the range of 1:1 to 1:100.

The ribonucleoside derivative represented by General Formula (II) can be produced by reacting a ribonucleoside derivative represented by General Formula (I) with an amine.

Examples of the amine used include methylamine, ethylamine, dimethylamine, and diethylamine.

The reaction is carried out in a solvent that does not inhibit the reaction. Examples of such a solvent include ethanol, methanol, and tetrahydrofuran.

The reaction temperature is not particularly limited, but is preferably within the range of 0 to 100° C.

The reaction time is not particularly limited, but is preferably 1 to 48 hours.

The amount ratio of the ribonucleoside derivative and the amine used in the reaction is not particularly limited, but the reaction is preferably carried out at a molar ratio of the ribonucleoside derivative to the amine within the range of 1:1 to 1:1000.

The nucleic acid derivative of the present invention is represented by General Formula (VI).

$B^1$, $B^2$, and $B^3$ in General Formula (VI) are the same or different and each represents a nucleic acid base residue optionally having a protecting group or a modifying group, and repeated n $B^2$s may be different. The nucleic acid base residue optionally having a protecting group or a modifying group represents the same groups as those of B.

$X^1$, $X^2$, and $X^3$ in General Formula (VI) are the same or different and each represents a hydrogen atom, a hydroxyl group, a methoxy group, a group expressed by General Formula (VII), or a group expressed by General Formula (VIII); and repeated n $X^2$s may be different.

n in General Formula (VI) represents an integer of 1 or more and is preferably an integer of 1 to 200 and more preferably an integer of 8 to 100.

$X^1$, $X^2$, and $X^3$ in General Formula (VI) may be the same groups described above with proviso that at least one of them is a group expressed by General Formula (VII) or General Formula (VIII). In n groups represented by $X^2$, 5 to 100% of the n groups are preferably those represented by General Formula (VII) or General Formula (VIII). $R^3$ to $R^5$ in General Formulae (VII) and (VIII) represent the same groups described above.

The nucleic acid derivative of the present invention can be synthesized by a known nucleic acid synthesis method (for example, a phosphoramidite method) from the above-described ribonucleoside derivative of the present invention.

The present invention also includes a method for preparing a ribonucleoside derivative represented by General Formula (IV) or a nucleic acid derivative containing the ribonucleoside derivative as a constituent by treating a ribonucleoside derivative represented by General Formula (I) or (II) (where $R^4$ and $R^5$ represent a group other than a hydrogen atom) or a nucleic acid derivative containing the ribonucleoside derivative as a constituent with a reagent containing a fluoride ion. In this

EXAMPLES

The present invention will now be described in further detail with reference to Examples.

Example 1

N³-Benzoyl-2'-O-(2-methoxycarbonylethyl)-3',5'-O-(1,1,3,3-tetraisopropyldisiloxane-1,3-diyl)uridine

[Formula 31]

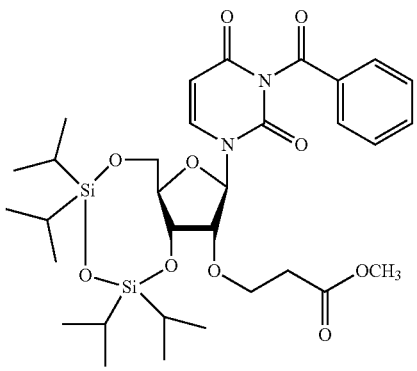

A literature known N³-benzoyl-3',5'-O-(1,1,3,3-tetraisopropyldisiloxane-1,3-diyl)uridine (1.80 g, 3.03 mmol) was dissolved in tert-butyl alcohol (15 mL). To the solution were added methyl acrylate (5.4 mL, 60.2 mmol) and cesium carbonate (489 mg, 1.39 mmol), followed by vigorous stirring at room temperature for 4 hours. Then, the reaction solution was filtered through Celite. The solvent and excess reagents were evaporated under reduced pressure. The resulting residue was subjected to silica gel column chromatography eluting with hexane-ethyl acetate (9:1, v/v) to give the title compound as a white foam-like material (1.47 g, 71%).

¹H NMR (CDCl₃, 500 MHz) δ 0.97-1.11 (28H, m), 2.58-2.60 (2H, m), 3.62 (3H, s), 3.88 (1H, d, J=4.15), 4.00 (1H, dd, J=2.44, 13.67), 4.02-4.27 (6H, m), 5.75 (1H, s), 5.77 (1H, d, J=8.06), 7.48-7.94 (5H, m), 8.00 (1H, d, J=8.06); ¹³C NMR (CDCl₃, 500 MHz) δ 12.6, 13.0, 13.2, 13.6, 17.0, 17.1, 17.3, 17.4, 17.6, 35.2, 51.7, 59.5, 66.7, 68.2, 81.9, 82.6, 89.2, 101.6, 129.3, 130.7, 131.4, 135.4, 139.3, 149.1, 162.3, 168.9, 171.7. HRMS calcd for C₃₂H₄₈N₂O₁₀Si₂ (M+H+): 677.2926. Found 677.2931.

Example 2

2'-O-(2-Methoxycarbonylethyl)-3',5'-O-(1,1,3,3-tetraisopropyldisiloxane-1,3-diyl)uridine

[Formula 32]

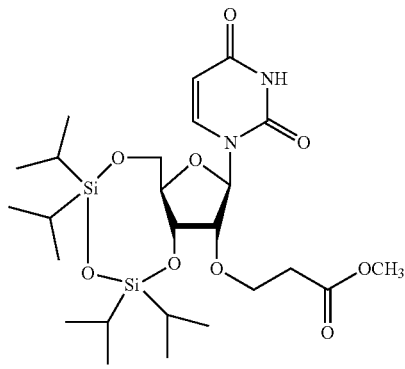

N³-Benzoyl-3',5'-O-(1,1,3,3-tetraisopropyldisiloxane-1,3-diyl)uridine (1494 mg, 2.53 mmol) was dissolved in tert-butyl alcohol (15 mL). To the resulting solution were added methyl acrylate (5.4 mL, 60.2 mmol) and cesium carbonate (489 mg, 1.38 mmol), followed by vigorous stirring at room temperature for 14 hours. Then, the reaction solution was filtered through Celite. The solvent and excess reagents were evaporated under reduced pressure. The resulting residue was dissolved in dehydrated tetrahydrofuran (15 mL). To the solution was added n-propylamine (1.5 mL, 18.0 mmol), followed by stirring for 1 hour. The solvent and excess reagents were evaporated under reduced pressure. The resulting residue was subjected to silica gel column chromatography eluting with hexane-ethyl acetate (3:1, v/v) to give the title compound as a white foam-like material (1030 mg, 71%).

¹H NMR (CDCl₃, 500 MHz) δ 0.92-1.09 (28H, m), 2.63-2.67 (2H, m), 3.68 (3H, s), 3.83 (1H, d, J=4.15), 3.93 (1H, dd, J=2.20, 13.43), 4.08-4.11 (3H, m) 4.13 (1H, dd, J=4.15, 9.78), 4.23-4.21 (1H, m), 5.66 (1H, d, J=8.06), 5.73 (1H, s), 7.88 (1H, d, J=8.06); ¹³C NMR (CDCl₃, 500 MHz) δ 12.6, 13.0, 13.2, 13.5, 17.0, 17.1, 17.2, 17.3, 17.4, 17.5, 17.6, 35.2, 51.8, 59.5, 66.8, 68.3, 81.7, 82.7, 89.0, 101.6, 139.7, 150.1, 163.9, 171.9.

Example 3

2'-O-[2-(N-Methylcarbamoyl)ethyl]-3',5'-O-(1,1,3,3-tetraisopropyldisiloxane-1,3-diyl)uridine

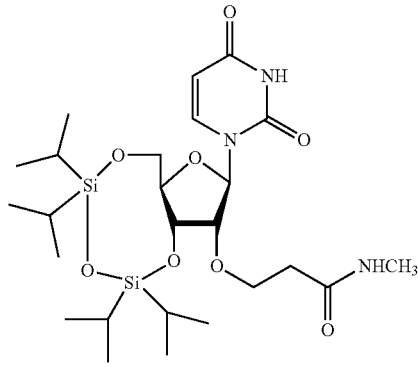

[Formula 33]

N³-Benzoyl-3',5'-O-(1,1,3,3-tetraisopropyldisiloxane-1,3-diyl)uridine (1.80 g, 3.03 mmol) was dissolved in tert-butyl alcohol (15 mL). To the solution were added methyl acrylate (5.4 mL, 60.2 mmol) and cesium carbonate (489 mg, 1.39 mmol), followed by vigorous stirring at room temperature for 4 hours. Then, the reaction solution was filtered through Celite. The solvent and excess reagents were evaporated under reduced pressure. The resulting residue was dissolved in a 40% methylamine-methanol solution (30 mL), followed by stirring at room temperature for 2 hours. Then, the solvent and excess reagents were evaporated under reduced pressure. The resulting residue was subjected to silica gel column chromatography eluting with hexane-ethyl acetate (4:1, 2:1, v/v) to give the title compound as a white foam-like material (1.14 g, 66%).

¹H NMR (CDCl₃, 500 MHz) ϵ 0.94-1.15 (28H, m), 2.47-2.63 (2H, m), 2.79-2.81 (3H, m), 3.85-4.29 (7H, m), 5.71-5.73 (2H, m), 6.90 (1H, br), 7.91 (1H, d, J=8.06), 9.90 (1H, br); ¹³C NMR (CDCl₃, 500 MHz) δ 12.5, 13.0, 13.1, 13.6, 16.9, 17.0, 17.1, 17.2, 17.3, 17.4, 17.5, 17.6, 23.0, 26.3, 36.6, 59.4, 67.7, 68.1, 82.0, 82.4, 88.9, 102.0, 139.3, 150.4, 163.8, 172.3. HRMS calcd for $C_{25}H_{45}N_3O_8Si_2$ (M+H+): 572.2823. Found 572.2826.

Example 4

2'-O-[2-(N-Methylcarbamoyl)ethyl]-3',5'-O-(1,1,3,3-tetraisopropyldisiloxane-1,3-diyl)adenosine

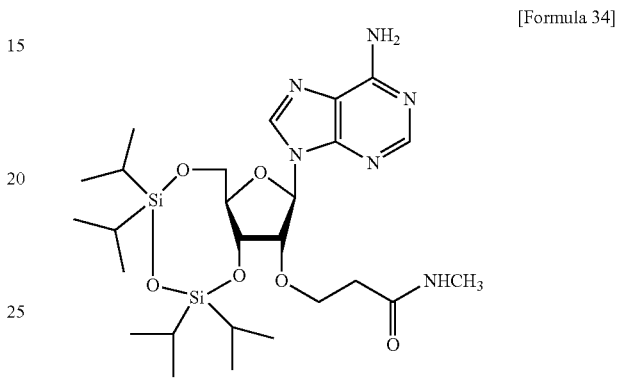

[Formula 34]

A literature known 6-N-dimethylaminomethylene-3',5'-O-(1,1,3,3-tetraisopropyldisiloxane-1,3-diyl)adenosine (1.62 g, 2.87 mmol) was dissolved in tert-butyl alcohol (15 mL). To the solution were added methyl acrylate (5.2 mL, 58 mmol) and cesium carbonate (94 mg, 0.29 mmol), followed by vigorous stirring at room temperature for 20 hours. The reaction system was filtered through Celite, and the filtrate was evaporated under reduced pressure.

To the residue was added a 40% methylamine/ethanol (30 mL), followed by stirring at room temperature for 6 hours. The reaction system was concentrated under reduced pressure. The residue was subjected to silica gel column chromatography eluting with chloroform:methanol (99.5:0.5, v/v) to give the title compound as a white solid (1.1 g, 67%).

¹H NMR (CDCl₃, 500 MHz) δ 0.94-1.24 (28H, m), 2.43-2.47 (1H, m), 2.65-2.70 (1H, m), 2.82-2.81 (3H, m), 3.99-4.04 (2H, m), 4.12-4.22 (4H, m), 4.61 (1H, dd, J=4.64, 9.28), 5.87 (2H, br), 6.01 (1H, s), 7.28-7.29 (1H, br), 8.15 (1H, s), 8.31 (1H, s); ¹³C NMR (CDCl₃) δ 12.6, 13.0, 13.1, 13.6, 16.9, 17.0, 17.1, 17.2, 17.3, 17.4, 17.5, 17.6, 26.4, 36.7, 59.7, 68.1, 69.0, 81.7, 82.0, 88.8, 120.6, 138.5, 148.9, 153.1, 155.7, 172.1. HRMS calcd for $C_{26}H_{46}N_6O_6Si_2$ (M+H+): 595.3026. Found 595.3093.

Example 5

2'-O-[2-(Methoxycarbonyl)ethyl]uridine

[Formula 35]

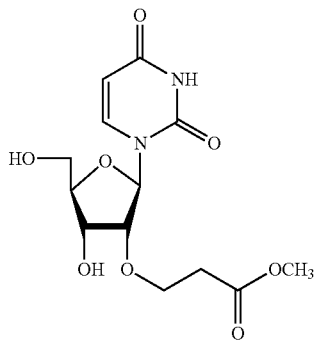

The compound (332 mg, 0.50 mmol) prepared in Example 1 was dissolved in dried tetrahydrofuran (5 mL). To the solution was added n-propylamine (183 μL, 2.2 mmol), followed by stirring at room temperature for 1 hour. The solvent was evaporated under reduced pressure, and the residue was dissolved in dried tetrahydrofuran (2 mL). To the reaction system were added triethylamine trihydrofluoride (248 μL, 1.54 mmol) and triethylamine (108 μL, 0.77 mmol), followed by stirring at room temperature for 1 hour. The solvent was evaporated under reduced pressure, and the residue was subjected to silica gel column chromatography eluting with chloroform:methanol (99:1, v/v) to give the title compound (183 mg, 96%).

$^1$H NMR (D$_2$O, 500 MHz) δ 2.70-2.73 (2H, m), 3.72 (3H, s), 3.80 (1H, dd, J=4.40, 12.94), 3.90-4.00 (4H, m), 4.12-4.14 (1H, m), 4.17 (1H, m), 4.32 (1H, t, J=5.37), 5.93 (1H, d, J=8.06), 5.97 (1H, d, J=4.40), 7.90 (1H, d, J=8.06); $^{13}$C NMR (D$_2$O) δ 35.0, 52.8, 61.1, 66.8, 68.9, 82.0, 85.1, 88.1, 102.9, 142.3, 152.0, 166.7, 175.2; HRMS calcd for C$_{13}$H$_{19}$N$_3$O$_7$ (M+H+) 331.1141. Found 331.1143.

Example 6

2'-O-[2-(N-Methylcarbamoyl)ethyl]uridine

[Formula 36]

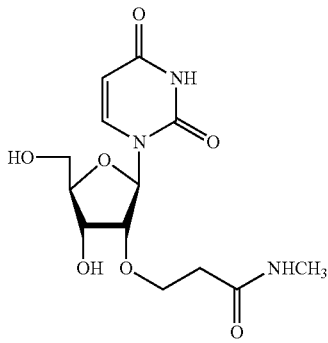

The compound (563 mg, 0.98 mmol) prepared in Example 3 was dissolved in dried tetrahydrofuran (2 mL). To the solution were added triethylamine trihydrofluoride (570 μL, 3.50 mmol) and triethylamine (253 μL, 1.80 mmol), followed by stirring at room temperature for 30 minutes. The reaction system was diluted with water and washed with ethyl acetate. The aqueous layer was concentrated through DowX (H+ form) to give the title compound (250 mg, 73%).

$^1$H NMR (D$_2$O, 500 MHz) δ 2.53-2.57 (2H, m), 2.68-2.72 (3H, m), (1H, dd, J=4.40, 12.94), 3.88-3.98 (3H, m), 4.12-4.17 (2H, m), 4.33 (1H, t, J=5.40), 5.92 (1H, d, J=8.30), (1H, d, J=4.64); $^{13}$C NMR (D$_2$O) δ 26.4, 36.5, 61.1, 67.2, 68.9, 81.8, 85.1, 88.2, 102.9, 142.3, 152.0, 166.7, 175.0; HRMS calcd for C$_{13}$H$_{19}$N$_3$O$_7$ (M+H+) 330.1301. found 330.1307.

Example 7

2'-O-[2-(N-Methylcarbamoyl)ethyl]adenosine

[Formula 37]

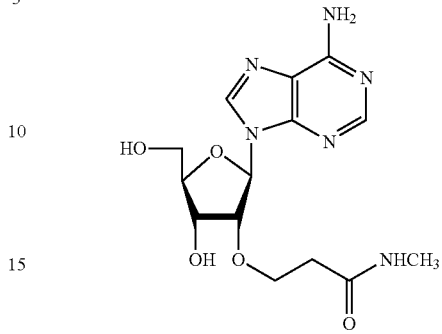

The compound (191 mg, 0.32 mmol) prepared in Example 4 was dissolved in dried tetrahydrofuran (3 mL). To the solution were added triethylamine trihydrofluoride (182 μL, 1.12 mmol) and triethylamine (81 μL, 0.58 mmol), followed by stirring at room temperature for 1 hour. The reaction system was diluted with water and washed with ethyl acetate. Crystals of the title compound (44 mg, 39%) were collected by filtration.

$^1$H NMR (D$_2$O, 500 MHz) δ 2.40-2.43 (2H, m), 2.47 (3H, s), 3.71-3.76 (1H, m), 3.86 (1H, dd, J=3.42, 12.67), 3.92-4.00 (2H, m), 4.34-4.36 (1H, m), 4.58 (1H, dd, J=2.44, 5.12), 4.61 (1H, dd, J=5.12, 6.83), 6.09 (1H, d, J=6.83), 8.29 (1H, s), 8.34 (1H, s); $^{13}$C NMR (D$_2$O) HRMS calcd for C$_{14}$H$_{20}$N$_6$O$_5$ (M+Na+) 375.1393. found 375.1347.

Example 8

5'-O-(4,4'-Dimethoxytrityl)-2'-O-[2-(N-methylcarbamoyl)ethyl]uridine

[Formula 38]

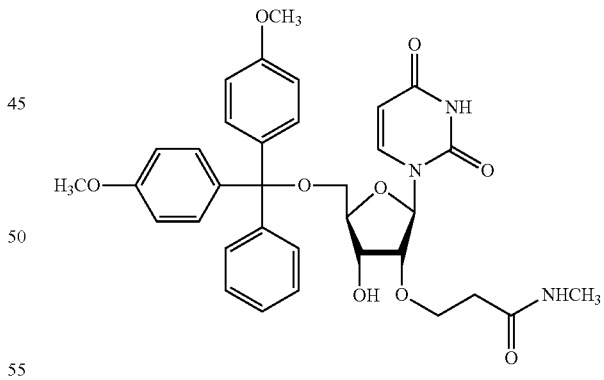

The compound (558 mg, 1.67 mmol) prepared in Example 6 was dissolved in dried pyridine (8 mL). To the solution was added 4,4'-dimethoxytrityl chloride (622 mg, 1.84 mmol), followed by stirring at room temperature. The reaction system was concentrated under reduced pressure, diluted with ethyl acetate, and then washed with a saturated sodium hydrogen carbonate aqueous solution. The organic layer was dried with anhydrous sodium sulfate and filtered. The filtrate was concentrated under reduced pressure. The residue was subjected to silica gel column chromatography eluting with chloroform:methanol (98:2, v/v) containing 0.5% triethylamine to give the title compound (749 mg, 70%).

$^1$H NMR (CDCl$_3$, 500 MHz) δ 2.43-2.61 (2H, m), 2.81 (3H, m), 3.48-3.54 (2H, m), 3.79 (3H, s), 3.90-3.97 (2H, m), 5.23 (1H, d, J=8.06), 5.86 (1H, br), 5.93 (1H, d, J=2.93), 6.83-6.86 (4H, m), 7.22-7.39 (9H, m), 7.95 (1H, d, J=8.06); $^{13}$C NMR (CDCl$_3$) δ 26.5, 35.9, 55.4, 62.1, 66.6, 69.2, 82.9, 83.7, 87.2, 87.9, 102.4, 113.4, 127.3, 128.1, 128.3, 130.2, 130.3, 135.3, 135.5, 140.3, 144.5, 150.8, 158.8, 163.6, 172.2; HRMS calcd for C$_{34}$H$_{37}$N$_3$O$_9$ (M+Na+) 654.2427. Found 654.2446.

Example 9

Stability of 2-(N-methylcarbamoyl)ethyl group to tetrabutylammonium fluoride

To the compound (4 mg, 0.01 mmol) synthesized in Example 8 were added 1M tetrabutylammonium fluoride/THF (1 mL), and the reaction was carried out at room temperature for 6 days. No degradation was observed in the analysis of the compound by silica gel thin layer chromatography (developing solvent:chloroform-methanol, 3:1, v/v). The compound was thus stable.

Example 10

5'-O-(4,4'-Dimethoxytrityl)-2'-O-[2-(N-methylcarbamoyl)ethyl]uridine 3'-(2-cyanoethyl N,N-diisopropylphosphoramidite)

[Formula 39]

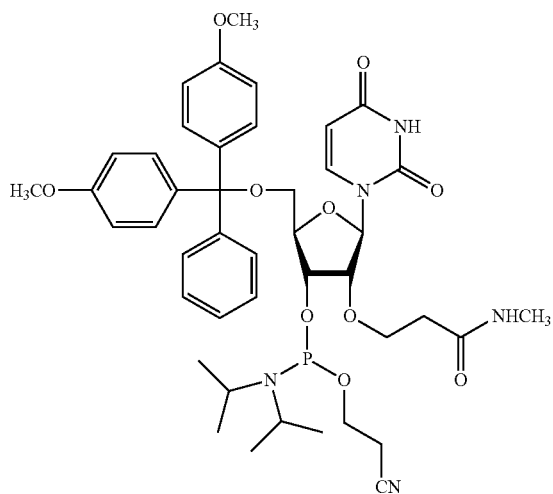

The compound (490 mg, 0.77 mmol) prepared in Example 8 was dissolved in dried acetonitrile (2 mL), and 2-cyanoethoxy N,N,N',N'-tetraisopropylphosphorodiamidite (358 mg, 1.19 mmol) dissolved in dried acetonitrile (2 mL) was added thereto. To the mixture was further added diisopropylammonium 1H-tetrazolide (101 mg, 0.59 mmol), followed by stirring at room temperature for 8 hours. The reaction was terminated by adding water thereto, and dilution with ethyl acetate was carried out. The organic layer was washed with saturated brine three times and a saturated sodium hydrogen carbonate aqueous solution three times. The organic layer was dried with anhydrous sodium sulfate and filtered. The filtrate was concentrated under reduced pressure. The residue was subjected to silica gel column chromatography eluting with chloroform:methanol (99:1, v/v) containing 0.5% triethylamine to give the title compound (384 mg, 66%).

$^1$H NMR (CDCl$_3$, 500 MHz) δ 1.03-1.29 (12H, m), 2.42-2.64 (4H, m), 2.77-2.80 (3H, m), 3.43-3.75 (6H, m), 3.79-3.80 (6H, m), 3.86-4.25 (4H, m), 4.48-4.61 (1H, m), 5.21-5.28 (1H, m), 5.90 (1H, m), 6.49 (1H, br), 6.82-6.85 (4H, m), 7.27-7.47 (9H, m), 8.01-8.09 (1H, m); $^{13}$C NMR (CDCl$_3$) δ 20.3, 20.4, 20.5, 21.5, 24.5, 24.6, 24.7, 24.6, 24.7, 24.8, 26.3, 36.9, 43.2, 43.3, 45.9, 55.3, 57.8, 58.0, 58.1, 60.5, 60.8, 67.7, 67.8, 69.4, 70.2, 81.8, 81.9, 82.0, 82.1, 82.2, 82.3, 87.0, 87.1, 88.8, 89.1, 102.3, 113.3, 117.6, 117.9, 127.2, 127.3, 128.0, 128.3, 130.3, 135.0, 135.1, 135.2, 140.0, 144.2, 144.3, 150.9, 151.0, 158.7, 158.8, 163.8, 163.9, 171.8, 171.9; $^{31}$P NMR (CDCl$_3$) δ 151.3, 150.5; HRMS calcd for C$_{43}$H$_{54}$N$_5$O$_{10}$P (M+H+) 832.3687. Found 832.3650.

Example 11

Synthesis of Oligonucleotide

[Formula 40]

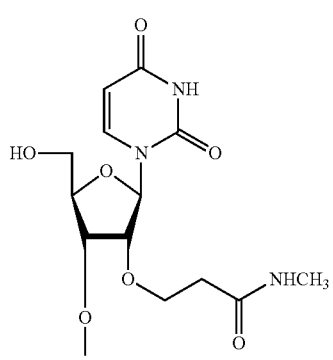

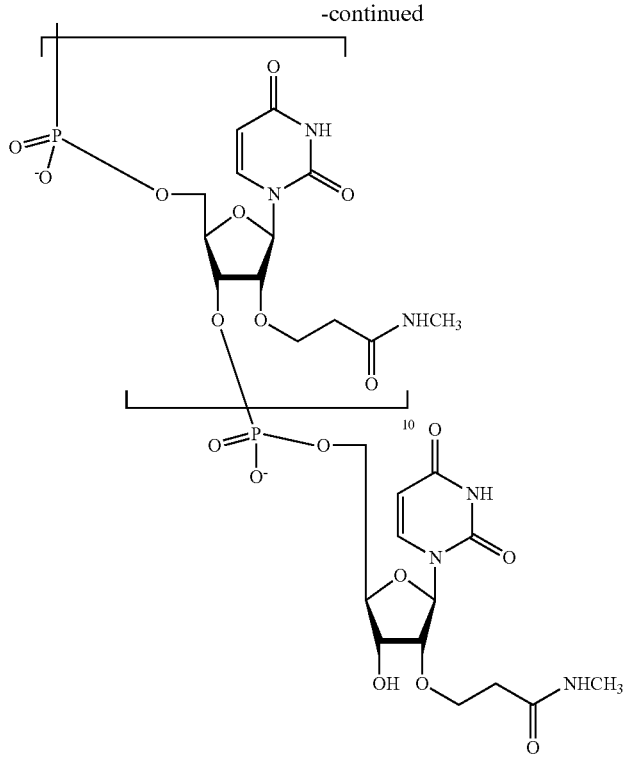

The synthesized oligonucleotide is a dodecamer having a sequence of $(U^*)_{12}$. $U^*$ in this oligonucleotide represents a 2'-O-[2-(N-methylcarbamoyl)ethyl]uridine residue. The oligonucleotide was synthesized on a solid support (Universal Support II: Glen Research) using an Applied Biosystems 392 oligonucleotide synthesizer in a 1-µmol scale. The phosphoramidite synthesized in Example 10 was dissolved in dried acetonitrile in a concentration of 0.1 M, and the solution was loaded on the oligonucleotide synthesizer. The synthesis was carried out according to the standard RNA synthesis protocol (tritylone) of the above-mentioned synthesizer except that the phosphoramidite-activating agent was 0.25 M 5-benzylthio-1H-tetrazole and condensation time was extended to 10 minutes. After the completion of oligonucleotide chain elongation, the solid support was immersed in 2M ammonia/methanol and was left at room temperature for 6 hours. The supernatant was concentrated under reduced pressure, and the residue was subjected to a C18 reverse-phase cartridge column to remove by-products. A 2% trifluoroacetic acid aqueous solution was loaded on the column to eliminate the dimethoxytrityl group, and then the objective substance was eluted with distilled water containing acetonitrile. The eluate was concentrated under reduced pressure, and the residue was purified with ion-exchange HPLC to give the objective substance in an isolation yield of 11%. The ion-exchange HPLC was carried out using a GenPak Fax column and an eluting solution of 25 mM sodium phosphate (pH 6.0) and 1 M NaCl with a gradient of 1% per minute at a column temperature of 50° C. and a flow rate of 1 mL/min.

Example 12

Elimination of 2-methoxycarbonyl Group with Tetrabutylammonium Fluoride

To the compound (4 mg, 0.01 mmol) synthesized in Example 5 was added 1 M tetrabutylammonium fluoride/ THF (1 mL) for a reaction at room temperature for 10 minutes. Complete conversion to uridine (Rf value: 0.32) was observed by silica gel thin layer chromatography (developing solvent:chloroform-methanol, 3:1, v/v) analysis.

Example 13

$N^3$-Benzoyl-3',5'-O-(1,1,3,3-tetraisopropyldisiloxane-1,3-diyl)-2'-O-[2-(2,2,2-trifluoroethoxy)carbonylethyl]uridine

[Formula 41]

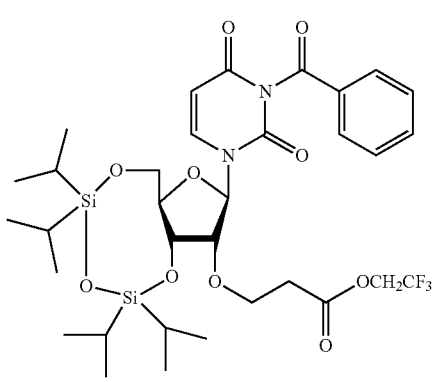

A literature known $N^3$-benzoyl-3',5'-O-(1,1,3,3-tetraisopropyldisiloxane-1,3-diyl)uridine (591 mg, 1 mmol) was dissolved in tert-butyl alcohol (5 mL). To the solution was added cesium carbonate (162 mg, 0.5 mmol) and then trifluoroethyl acrylate (2.5 mL, 20 mmol), followed by vigorous stirring at room temperature for 3 hours. The reaction solution was filtered through Celite. The solvent and excess reagents were evaporated under reduced pressure, and the resulting residue was subjected to silica gel column chromatography eluting with hexane-ethyl acetate (5:1, v/v) to give the title compound as a white foam-like material (387 mg, 53%).

$^1$H NMR (CDCl$_3$, 500 MHz) δ 0.96-1.11 (28H, m), 2.67-2.69 (2H, m), 3.62 (3H, s), 3.90 (1H, d, J=4.15 Hz), 3.96 (1H, dd, J=13.4, 2.0 Hz), 4.06 (2H, m), 4.10 (1H, dd, J=9.5 Hz, 1.5 Hz), 4.18 (1H, m), 4.25 (1H, d, J=13.4 Hz), 4.40 (1H, m), 5.72 (1H, s), 5.77 (1H, d, J=8.3 Hz), 7.49 (2H, m), 7.64 (1H, m), 7.92 (2H, m), 7.99 (1H, d, J=8.3 Hz)

Example 14

N$^3$-Benzoyl-2'-O-[2-(2,2,2-trifluoroethoxy)carbonyl-ethyl]uridine

[Formula 42]

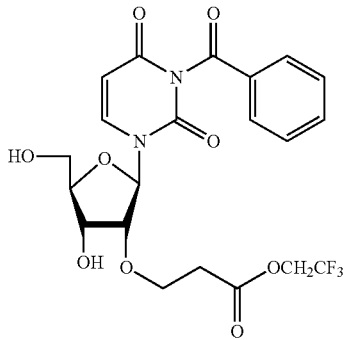

N$^3$-Benzoyl-3',5'-O-(1,1,3,3-tetraisopropyldisiloxane-1,3-diyl)-2'-O-[2-(2,2,2-trifluoroethoxy)carbonylethyl]uridine (1.5 g, 2 mmol) synthesized in Example 13 was dissolved in tetrahydrofuran (8 mL). To this solution were added triethylamine (780 μL, 3.5 mmol) and then triethylamine trihydrofluoride (1.1 mL, 7 mmol), followed by stirring at room temperature for 30 minutes. Then, the solvent was evaporated under reduced pressure. The resulting residue was subjected to silica gel column chromatography eluting with chloroform:methanol (100:1, v/v) to give the title compound as a white foam-like material (803 mg, 80%).

$^1$H NMR (CDCl$_3$, 500 MHz) δ 3.79-2.65 (3H, m), 3.70 (1H, s), 4.13-3.80 (6H, m), 4.34 (1H, t, J=0.01), 4.52-4.49 (2H, m), 5.82-5.77 (2H, m), 7.52-7.48 (1H, m), 7.68-7.64 (1H, m), 7.94-7.92 (1H, m), 7.97 (1H, d, J=0.03).

Example 15

N$^3$-Benzoyl-5'-O-(4,4'-dimethoxytrityl)-2'-O-[2-(2,2,2-trifluoroethoxy)carbonylethyl]uridine

[Formula 43]

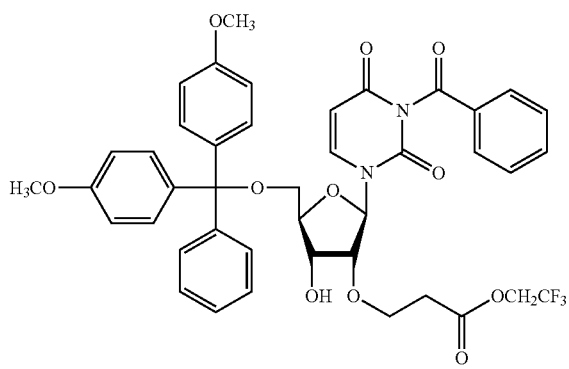

The N$^3$-benzoyl-2'-O-[2-(2,2,2-trifluoroethoxy)carbonyl-ethyl]uridine (750 mg, 1.5 mmol) synthesized in Example 14 was dissolved in dried pyridine (15 mL). To the solution was added 4,4'-dimethoxytrityl chloride (763 mg, 2.3 mmol), followed by stirring at room temperature for 1.5 hours. The reaction was terminated by adding water thereto. The solvent was evaporated under reduced pressure, and the residue was subjected to silica gel column chromatography eluting with hexane-chloroform (1:1, v/v) to give the title compound as a white foam-like material (750 mg, 62%).

$^1$H NMR (CDCl$_3$, 500 MHz) δ 2.52-2.79 (2H, m), 3.57 (2H, m), 3.81 (6H, s), 3.90-3.96 (1H, m), 3.99-4.08 (2H, m), 4.13-4.17 (1H, m), 4.44-4.59 (2H, m), 5.37 (1H, d, J=8.3 Hz), 5.92 (1H, m), 6.86 (4H, d, J=8.79 Hz), 7.30-7.34 (7H, m), 7.40 (2H, m), 7.50 (2H, m), 7.65 (1H, m), 7.95 (2H, m), 8.16 (1H, d, J=8.3 Hz)

Example 16

5'-O-(4,4'-Dimethoxytrityl)-2'-O-[2-(N,N-dimethyl-carbamoyl)ethyl]uridine

[Formula 44]

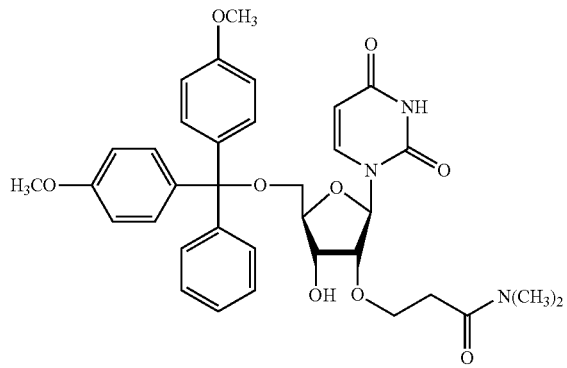

To N$^3$-benzoyl-5'-O-(4,4'-dimethoxytrityl)-2'-O-[2-(2,2,2-trifluoroethoxy)carbonylethyl]uridine (120 mg, 0.15 mmol) synthesized in Example 15 was added 2 M dimethylamine/tetrahydrofuran (4 mL), followed by stirring at room temperature for 15 hours. Then, the reaction was carried out at 40° C. for 2 hours. The solvent was evaporated under reduced pressure, and the residue was subjected to silica gel column chromatography eluting with chloroform to give the title compound as a white foam-like material (80 mg, 83%).

$^1$H NMR (CDCl$_3$, 500 MHz) δ 2.43 (1H, d, J=17.1 Hz), 2.78 (1H, ddd, J=3.2 Hz, 10.8 Hz, 17.1 Hz), 2.97 (3H, s), 3.01 (3H, s), 3.45 (1H, dd, J=2.2 Hz, 10.7 Hz), 3.52 (1H, dd, J=2.7 Hz, 10.7 Hz), 3.79 (3H, s), 3.89 (1H, m), 3.99 (1H, t, J=4.2 Hz), 4.10 (2H, m), 4.58 (1H, dd, J=5.9 Hz, 10.7 Hz), (1H, d, J=8.1 Hz), 5.35 (1H, d, J=6.6 Hz), 5.96 (1H, d, J=3.7 Hz), 6.83 (4H, d, J=8.5 Hz), 7.23-7.29 (7H, m), (2H, m), 7.92 (1H, d, J=8.30 Hz), 8.72 (1H, br).

Example 17

Elimination of 2-(N,N-dimethylcarbamoylethyl) Group with Tetrabutylammonium Fluoride To the compound (6 mg, 0.01 mmol) synthesized in Example 16 was added 1 M tetrabutylammonium fluoride/THF (1 mL), followed by a reaction at room temperature for 2 hours. Complete conversion to 5'-O-dimethoxytrityl uridine

Example 18

6-N-Acetyl-2'-O-(2-methylaminocarbonylethyl)-5'-O-dimethoxytrityladenosine

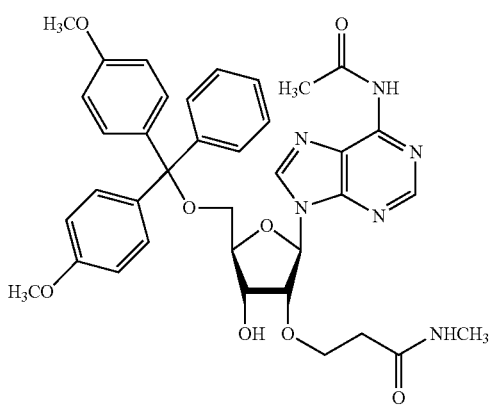

[Formula 45]

2'-O-[2-(N-Methylcarbamoyl)ethyl]-3',5'-O-(1,1,3,3-tetraisopropyldisiloxane-1,3-diyl)adenosine (7.20 g, 12.12 mmol) synthesized in Example 4 was dissolved in anhydrous pyridine (120 mL). To the solution was added acetyl chloride (1 mL, 14.0 mmol), followed by stirring at room temperature for 5 hours. Then, the reaction was terminated by adding methanol thereto. The solvent and excess reagents were evaporated under reduced pressure. The resulting residue was diluted with chloroform and washed with saturated brine and saturated sodium hydrogen carbonate. The organic layer was dried with anhydrous sodium sulfate and then filtered. The solvent was evaporated under reduced pressure. The resulting residue was dissolved in anhydrous THF, and triethylamine trihydrofluoride (6.9 mL, 42.37 mmol) and triethylamine (3 mL, 21.93 mmol) were added thereto, followed by stirring at room temperature for 1 hour. Then, the solvent was evaporated under reduced pressure, and the resulting residue was subjected to adsorption to silica gel column chromatography and eluted with chloroform-methanol (100:0, 98:2, 96:4, v/v) for rough purification. The resulting residue was azeotropically dehydrated with anhydrous pyridine four times and was dissolved in 100 mL of anhydrous pyridine. Dimethoxytrityl chloride (4.1 g, 12.13 mmol) was added to the reaction solution, followed by stirring at room temperature for 1 hour. Then, the reaction was terminated by the addition of methanol, and the solvent was evaporated under reduced pressure. The resulting residue was dissolved in chloroform, washed with saturated brine and a saturated sodium hydrogen carbonate aqueous solution, and dried with anhydrous sodium sulfate. The solvent was evaporated under reduced pressure, and the resulting residue was subjected to adsorption to silica gel column chromatography and eluted with chloroform-methanol (99:1, 98:2, 97:3, v/v, 0.5% triethylamine) to give the title compound as a white foam-like material (4.67 g, 55%).

$^1$H NMR (CDCl$_3$, 500 MHz) δ 2.29-2.47 (2H, m), 2.51 (3H, s), 2.73-2.74 (3H, m), 3.33-3.40 (2H, m), 3.66-3.71 (7H, m), 3.94-3.99 (1H, m), 4.21-4.24 (1H, m), 4.54-4.63 (3H, m), (1H, m), 6.05 (1H, d, J=5.62), 6.71-6.73 (4H, m), (9H, m), 8.10 (1H, s), 8.51 (1H, s), 8.73 (1H, br)

Example 19

6-N-Acetyl-2'-O-(2-methylaminocarbonylethyl)-5'-O-dimethoxytrityladenosine 3'-(2-cyanoethyl N,N-diisopropylphosphoramidite)

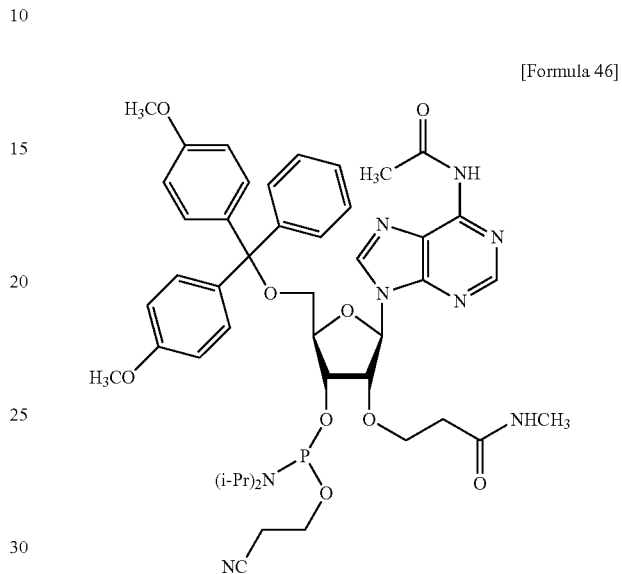

[Formula 46]

6-N-Acetyl-2'-O-(2-methylaminocarbonylethyl)-5'-O-dimethoxytrityladenosine (1.48 g, 2.12 mmol) was azeotropically dehydrated with anhydrous toluene three times for argon substitution. To the reaction system was added an anhydrous dichloromethane solution (1 mL) prepared by dissolving diisopropylethylamine (555 μL, 3.18 mmol) and 2-cyanoethyl-N,N-diisopropylaminochlorophosphine (551 mg, 2.33 mmol) in anhydrous dichloromethane. The mixture was stirred at room temperature for 2 hours and then diluted with chloroform and washed with saturated brine and a saturated sodium hydrogen carbonate aqueous solution. The organic layer was dried with anhydrous sodium sulfate, and the solvent was evaporated under reduced pressure. The resulting residue was subjected to adsorption to silica gel column chromatography and eluted with chloroform-methanol (100:1, 99:1, v/v, 0.5% triethylamine) to give the title compound as a white foam-like material (1107 mg, 58%).

$^1$H NMR (CDCl$_3$, 500 MHz) δ 1.04-1.18 (12H, m), 2.31-2.70 (10H, m), 3.34-3.37 (1H, m), 3.51-4.05 (17H, m), 4.33-4.41 (1H, m), 4.57-4.68 (1H, m), 6.15-6.16 (1H, m), 6.42-6.43 (1H, m), 6.77-6.81 (4H, m), 7.18-7.42 (9H, m), 8.26-8.30 (1H, m), 8.60-8.62 (1H, m), 8.97 (1H, br), 8.51 (1H, s), 8.73 (1H, br)

Example 20

Evaluation of Hybridization Ability of Synthesized Oligonucleotide

The Tm between the oligonucleotide synthesized in Example 11 and its complementary RNA chain, adenylic acid dodecamer (AAAAAAAAAAAA), was measured. Each oligonucleotide was dissolved in 10 mM sodium phosphate buffer (pH 7.0)/0.1 M NaCl in a concentration of 2 μM. This solution was heated to 70° C., maintained at this temperature for 15 minutes, then cooled to 5° C. at a rate of 1 degree per minute, and then heated to 70° C. again at the same rate. During this procedure, UV absorption at 260 nm was measured to obtain a UV melting curve. The obtained UV melting curve was differentiated, and the temperature at the maximum value was defined as the Tm value. The Tm value was 26° C.

Separately, the Tm between an uridylic acid dodecamer and an adenylic acid dodecamer was measured for comparison and was 14° C. It was thus revealed that the oligonucleotide synthesized in Example 11 had hybridization ability higher than that of a natural oligonucleotide.

Example 21

2'-O-[2-(N-Methylcarbamoyl)ethyl]-3'-5'-O-(1,1,3,3-tetraisopropyldisiloxane-1,3-diyl)cytidine

[Formula 39]

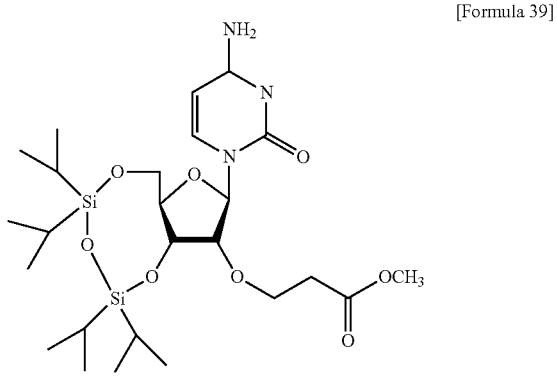

4-Dimethylformamidinyl-3',5'-O-(1,1,3,3,-tetraisopropyl-disiloxane-1,3-diyl)cytidine (6.64 mg, 12.3 mmol) was dissolved in tert-butyl alcohol (120 mL). To the solution were added methyl acrylate (23 mL, 246 mmol) and cesium carbonate (1.95 mg, 1.20 mmol), followed by vigorous stirring at room temperature for 4 hours. Then, the reaction solution was filtered through Celite. The solvent and excess reagents were evaporated under reduced pressure. The resulting residue was dissolved in 40% methylamine methanol solution (120 mL), followed by stirring at room temperature for 10 hours. Then, the solvent and excess reagents were evaporated under reduced pressure. The reaction product was subjected to NH-silica gel column chromatography eluting with a chloroform-methanol solution (99:1, 95:5, v/v) to give the title compound as a white foam-like material (2.50 g, 4.30 mmol).
$^1$H NMR (CDCl$_3$, 500 MHz) σ 0.86-1.06 (28H, m), 2.33-2.38 (2H, m), 2.58-2.64 (2H, m), 2.74-2.75 (3H, d), 3.84-4.22 (7H, m), 5.64 (1H, s), 5.78-5.79 (1H, d), 7.29-7.31 (1H, dd), 7.84-7.86 (1H, d)

Example 22

2'-O-[2-(N-Methylcarbamoyl)ethyl]-cytidine

[Formula 40]

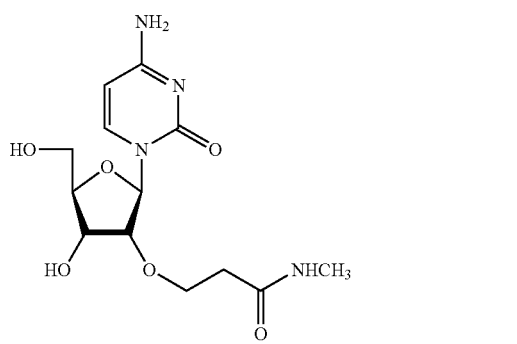

The compound (1.55 g, 2.72 mmol) prepared in Example 21 was dissolved in dried tetrahydrofuran (15 mL). To the solution was added triethylamine trihydrofluoride (1.55 mL, 1.65 mmol), followed by vigorous stirring at room temperature for 1 hour. The solvent and excess reagents were evaporated under reduced pressure, and the reaction product was subjected to NH-silica gel column chromatography eluting with a chloroform-methanol solution (80:20, 70:30, v/v) to give the title compound (600 mg, 1.82 mmol).
$^1$H NMR (DMSO, 500 MHz) σ 2.35-2.45 (2H, m), 2.59-2.60 (3H, d), 3.57-3.61 (1H, m), 3.67-3.69 (1H, s), 3.73-3.81 (2H, m), 3.83-3.85 (2H, m), 5.15-5.16 (2H, d), 5.73-5.76 (1H, d), 5.83-5.84 (1H, d), 7.21-7.23 (2H, d), 7.90-7.93 (2H, m)

Example 23

2'-O-[2-(N-Methylcarbamoyl)ethyl]-4-N-acetylcytidine

[Formula 41]

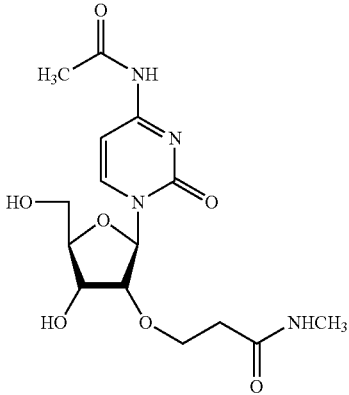

The compound (614 mg, 1.87 mmol) prepared in Example 22 was dissolved in ethanol (10 mL). To this solution was added anhydrous acetic acid (300 μL, 3.67 mmol), followed by vigorous stirring under reflux at 80° C. for 2 hours. The solvent and excess reagents were evaporated under reduced pressure. Reprecipitation with ethanol and ethyl acetate gave the title compound (625 mg, 1.69 mmol).
$^1$H NMR (DMSO, 500 MHz) σ 2.09 (3H, s), 2.33-2.39 (2H, m), 2.55-2.56 (3H, d), 3.63-4.08 (m), 5.21-5.26 (2H, m), 5.79-5.80 (1H, d), 7.17-7.19 (1H, d), 7.85-7.80 (1H, t), 8.41-8.43 (1H, d), 10.86 (1H, s)

Example 24

5'-O-(4,4'-Dimethoxytrityl)-2'-O-[2-(N-methylcarbamoyl)ethyl]-4-N-acetylcytidine

[Formula 42]

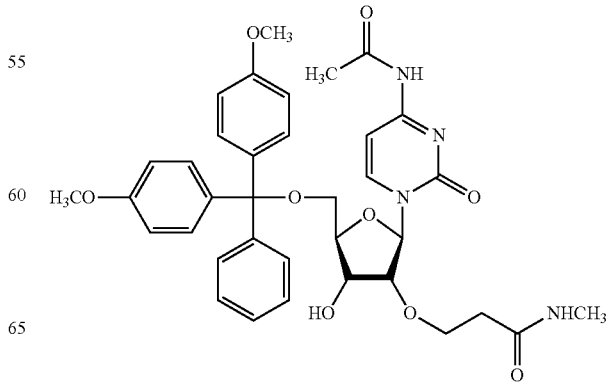

The compound (550 mg, 1.48 mmol) prepared in Example 23 was dissolved in dried pyridine (15 mL). To the solution was added 4,4'-dimethoxytrityl chloride (552 mg, 1.63 mmol), followed by vigorous stirring at room temperature for 2 hours. The reaction was terminated with a small amount of water, and the reaction system was concentrated under reduced pressure, diluted with chloroform, and washed with a saturated sodium hydrogen carbonate aqueous solution. The organic layer was dried with anhydrous sodium sulfate and was concentrated under reduced pressure. The residue was subjected to silica gel column chromatography eluting with chloroform:methanol:triethylamine (98:1.5:0.5) to give the title compound (445 mg, 1.00 mmol).

$^1$H NMR(CDCl$_3$, 500 MHz) σ 2.08 (1H, s), 2.18 (3H, s), 2.39-2.43 (1H, m), 2.53-2.61 (1H, m), 2.75-2.76 (3H, d), 3.54-3.55 (2H, d), 3.79-3.80 (6H, m), 3.92-3.93 (1H, d), 4.00-4.15 (3H, m), 4.45-4.49 (2H, m) 5.89 (1H, s), 6.52 (1H, s), 6.83-6.85 (3H, d), 7.10-7.11 (1H, s), 7.23-7.41 (8H, m), 8.47-8.49 (1H, d), 9.49 (1H, s)

Example 25

5'-O-(4,4'-Dimethoxytrityl)-2'-O-[2-(N-methylcarbamoyl)ethyl]-4-N-acetylcytidine 3'-(2-cyanoethyl N,N'-diisopropylphosphoramidite)

[Formula 43]

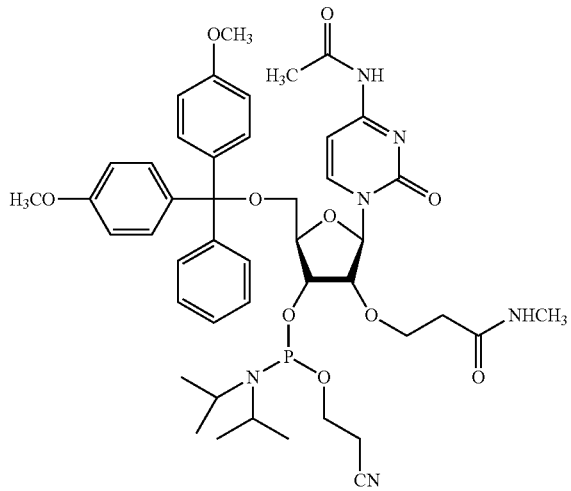

The compound (480 mg, 0.71 mmol) prepared in Example 24 was dissolved in dried acetonitrile (2 mL). To the solution was added 2-cyanoethoxy N,N,N',N'-tetraisopropylphosphorodiamidite (343 μL, 1.07 mmol) dissolved in dried acetonitrile (2 mL) and then diisopropylammonium 1H-tetrazolide (92 mg, 0.54 mmol), followed by vigorous stirring at room temperature for 15 hours. The reaction was terminated with a small amount of water, and then the reaction system was concentrated under reduced pressure, diluted with chloroform, and washed with saturated brine. The organic layer was dried with anhydrous sodium sulfate, and filtrate was concentrated under reduced pressure. The residue was subjected to silica gel column chromatography eluting with chloroform:methanol:triethylamine (98:1.5:0.5) to give the title compound (300 mg, 0.34 mmol).

$^1$H NMR (CDCl$_3$, 500 MHz) σ 0.99-1.23 (14H, m), 2.22-2.36 (3H, m), 2.37-2.41 (2H, m), 2.58-2.78 (5H, m), 3.45-3.79 (13H, m), 3.97-4.26 (4H, m), 4.40-4.54 (1H, m), 5.89-5.90 (1H, d), 6.82-7.43 (20H, m), 8.52-8.60 (1H, m), 10.13-12.16 (1H, d)

Example 26

Synthesis of Oligoribonucleotide

[Formula 44]

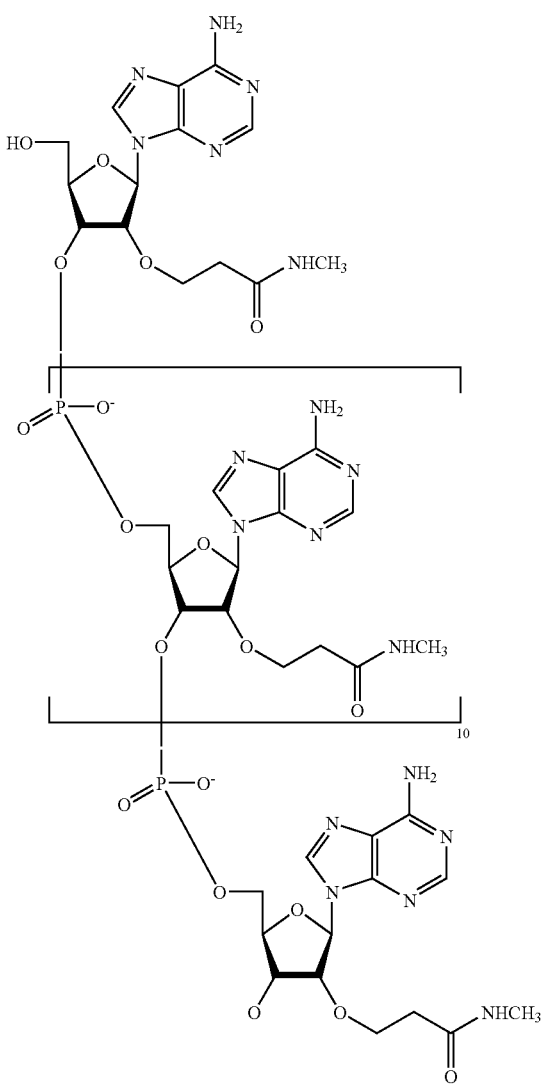

The synthesized oligonucleotide is a dodecamer having a sequence of (A*)$_{12}$. A* in this oligonucleotide represents a 2'-O-[2-(N-methylcarbamoyl)ethyl]adenosine residue. The title compound was prepared using the phosphoramidite synthesized in Example 19 by a method similar to that in Example 11.

Example 27

Resistance to Enzyme

The oligonucleotide (50 μmol) prepared in Example 11 was dissolved in 50 mM tris-hydrochloric acid buffer (990 μL, pH 8.5, 72 mM sodium chloride, 14 mM magnesium chloride). To the solution was added snake venom phosphodiesterase (Sigma-Aldrich) (2.5 µg, 5×10⁻⁴ units) dissolved in 50 mM tris-hydrochloric acid buffer (10 µL, pH 8.5, 72 mM sodium chloride, 14 mM magnesium chloride), followed by a reaction at 37° C. The enzyme reaction was terminated at 0° C., and then the reaction solution was diluted with pure water. The ratio of remaining full-length oligonucleotide was determined by anion-exchange chromatography. The ratios of remaining full-length oligonucleotide were 94%, 95%, 87%, 78%, 60%, and 41% after the reaction for 5 minutes, 10 minutes, 20 minutes, 40 minutes, 80 minutes, and 160 minutes, respectively.

This description includes the contents of Japanese Patent Application (Application No. 2006-063358), which is the base of the priority of this application. All the publications, patents, and patent applications cited in the present invention are incorporated herein by reference in their entireties.

The invention claimed is:

1. A ribonucleoside derivative represented by General Formula (I):

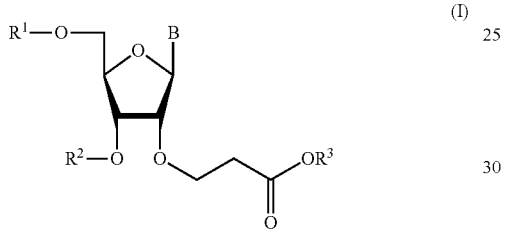

wherein $R^1$ represents a hydrogen atom or a protecting group for a hydroxyl group;
$R^2$ represents a hydrogen atom, a protecting group for a hydroxyl group, or a group expressed by General Formula (III):

wherein $R^6$ and $R^7$ are the same or different and each represents an alkyl group, or binds to each other to form a ring that optionally contains a hetero atom;
$R^8$ represents a protecting group for a phosphate group;
$R^3$ represents a hydrogen atom, an alkyl group optionally having a substituent, an aralkyl group optionally having a substituent, an alkenyl group optionally having a substituent, an alkynyl group optionally having a substituent, or an aryl group optionally having a substituent; and
B represents an adenine nucleic acid base optionally protected by one or two acyl groups or an amidine protecting group at the N6 position of the adenine amino group, a cytosine nucleic acid base, a guanine nucleic acid base optionally protected by one or two acyl groups or an amidine protecting group at the N2 position of the guanine amino group, a uracil nucleic acid base optionally protected by an alkyl group or an acyl group at the N3 position, a thymine nucleic acid base optionally protected by an alkyl group or an acyl group at the N3 position, or a pyrimidine base having an alkyl group, an alkynyl group, an aryl group, a fluorescent functional group, a biotinyl group, an amino group or a spin label at the 5-position.

2. The ribonucleoside derivative according to claim 1, wherein $R^3$ in General Formula (I) represents a methyl group or a 2,2,2-trifluoroethyl group.

3. A ribonucleoside derivative represented by General Formula (II):

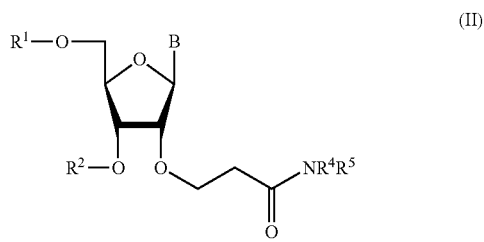

wherein $R^1$ represents a hydrogen atom or a protecting group for a hydroxyl group; $R^2$ represents a hydrogen atom, a protecting group for a hydroxyl group, or a group expressed by General Formula (III):

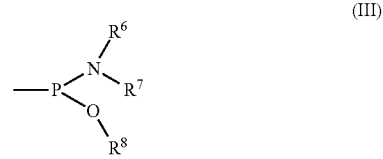

wherein $R^6$ and $R^7$ are the same or different and each represents an alkyl group, or binds to each other to form a ring that optionally contains a hetero atom;
$R^8$ represents a protecting group for a phosphate group;
$R^4$ and $R^5$ are the same or different and each represent a hydrogen atom, an alkyl group optionally having a substituent, an aralkyl group optionally having a substituent, an alkenyl group optionally having a substituent, an alkynyl group optionally having a substituent, or an aryl group optionally having a substituent; and
B represents an adenine nucleic acid base optionally protected by one or two acyl groups or an amidine protecting group at the N6 position of the adenine amino group, a cytosine nucleic acid base, a guanine nucleic acid base optionally protected by one or two acyl groups or an amidine protecting group at the N2 position of the guanine amino group, a uracil nucleic acid base optionally protected by an alkyl group or an acyl group at the N3 position, a thymine nucleic acid base optionally protected by an alkyl group or an acyl group at the N3 position, or a pyrimidine base having an alkyl group, an alkynyl group, an aryl group, a fluorescent functional group, a biotinyl group, an amino group or a spin label at the 5-position.

4. The ribonucleoside derivative according to claim 3, wherein $R^4$ and $R^5$ in General Formula (II) each represent a methyl group.

5. The ribonucleoside derivative according to claim 3, wherein at least one of $R^4$ and $R^5$ in General Formula (II) represents a hydrogen atom.

6. A process for producing a ribonucleoside derivative comprising:

reacting a ribonucleoside derivative represented by General Formula (IV):

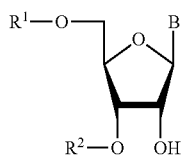

(IV)

wherein $R^1$ represents a hydrogen atom or a protecting group for a hydroxyl group;

$R^2$ represents a hydrogen atom, a protecting group for a hydroxyl group, or a group expressed by General Formula (III):

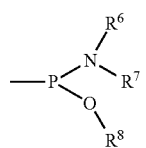

(III)

wherein $R^6$ and $R^7$ are the same or different and each represents an alkyl group, or binds to each other to form a ring that optionally contains a hetero atom;

$R^8$ represents a protecting group for a phosphate group; and

B represents an adenine nucleic acid base optionally protected by one or two acyl groups or an amidine protecting group at the N6 position of the adenine amino group, a cytosine nucleic acid base, a guanine nucleic acid base optionally protected by one or two acyl groups or an amidine protecting group at the N2 position of the guanine amino group, a uracil nucleic acid base optionally protected by an alkyl group or an acyl group at the N3 position, a thymine nucleic acid base optionally protected by an alkyl group or an acyl group at the N3 position, or a pyrimidine base having an alkyl group, an alkynyl group, an aryl group, a fluorescent functional group, a biotinyl group, an amino group or a spin label at the 5-position with an acrylic acid ester represented by General Formula (V):

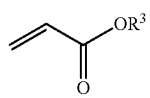

(V)

wherein $R^3$ represents a hydrogen atom, an alkyl group optionally having a substituent, an aralkyl group optionally having a substituent, an alkenyl group optionally having a substituent, an alkynyl group optionally having a substituent, or an aryl group optionally having a substituent to obtain a ribonucleoside derivative represented by General Formula (I):

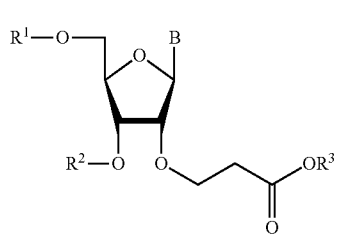

(I)

wherein $R^1$ represents a hydrogen atom or a protecting group for a hydroxyl group;

$R^2$ represents a hydrogen atom, a protecting group for a hydroxyl group, or a group expressed by General Formula (III);

B represents an adenine nucleic acid base optionally protected by one or two acyl groups or an amidine protecting group at the N6 position of the adenine amino group, a cytosine nucleic acid base, a guanine nucleic acid base optionally protected by one or two acyl groups or an amidine protecting group at the N2 position of the guanine amino group, a uracil nucleic acid base optionally protected by an alkyl group or an acyl group at the N3 position, a thymine nucleic acid base optionally protected by an alkyl group or an acyl group at the N3 position, or a pyrimidine base having an alkyl group, an alkynyl group, an aryl group, a fluorescent functional group, a biotinyl group, an amino group or a spin label at the 5-position with an acrylic acid ester represented by General Formula (V); and $R^3$ represents a hydrogen atom, an alkyl group optionally having a substituent, an aralkyl group optionally having a substituent, an alkenyl group optionally having a substituent, an alkynyl group optionally having a substituent, or an aryl group optionally having a substituent.

7. The process for producing a ribonucleoside derivative according to claim 6, wherein $R^3$ in General Formula (I) represents a methyl group or a 2,2,2-trifluoroethyl group.

8. A nucleic acid derivative represented by General Formula (VI):

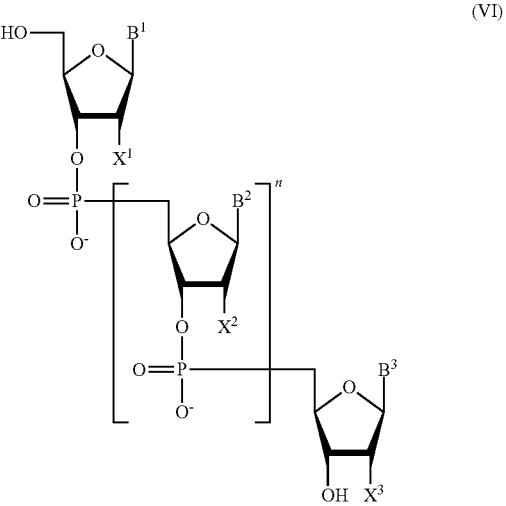

(VI)

wherein $B^1$, $B^2$, and $B^3$ are the same or different and each represents a nucleic acid base residue optionally having a protecting group or a modifying group; repeated n $B^2$s may be different; $X^1$, $X^2$, and $X^3$ are the same or different and each represents a hydrogen atom, a hydroxyl group, a methoxy group, a cyanoethoxy group, a group expressed by General Formula (VII):

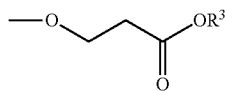

(VII)

wherein $R^3$ represents a hydrogen atom, an alkyl group optionally having a substituent, an aralkyl group optionally having a substituent, an alkenyl group optionally having a substituent, an alkynyl group optionally having a substituent, or an aryl group optionally having a substituent, or a group expressed by General Formula (VIII):

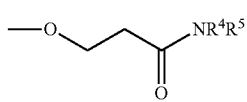

(VIII)

wherein $R^4$ and $R^5$ are the same or different and each represents a hydrogen atom, an alkyl group optionally having a substituent, an aralkyl group optionally having a substituent, an alkenyl group optionally having a substituent, an alkynyl group optionally having a substituent, or an aryl group optionally having a substituent; repeated n $X^2$s may be different; n is an integer of 1 or more; and at least one of $X^1$, $X^2$, and $X^3$ represents a group expressed by General Formula (VII) or (VIII).

9. The nucleic acid derivative according to claim 8, wherein $R^3$ in General Formula (VII) represents a methyl group or a 2,2,2-trifluoroethyl group.

10. The nucleic acid derivative according to claim 8, wherein $R^4$ and $R^5$ in General Formula (VIII) represent a methyl group.

11. The nucleic acid derivative according to claim 8, wherein at least one of $R^4$ and $R^5$ in General Formula (VIII) represents a hydrogen atom.

12. A process for preparing a ribonucleoside derivative or a nucleic acid derivative containing the ribonucleoside derivative as a constituent, the process comprising:
treating a ribonucleoside derivative represented by General Formula (I):

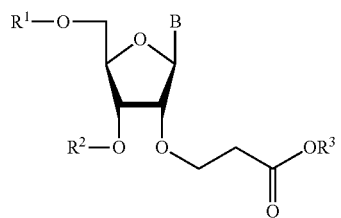

(I)

wherein $R^1$ represents a hydrogen atom or a protecting group for a hydroxyl group;

$R^2$ represents a hydrogen atom, a protecting group for a hydroxyl group, or a group expressed by General Formula (III):

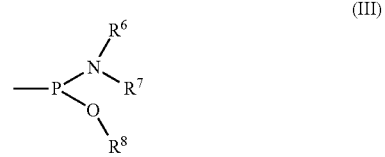

(III)

wherein $R^6$ and $R^7$ are the same or different and each represents an alkyl group, or binds to each other to form a ring that optionally contains a hetero atom;
$R^8$ represents a protecting group for a phosphate group;
$R^3$ represents a hydrogen atom, an alkyl group optionally having a substituent, an aralkyl group optionally having a substituent, an alkenyl group optionally having a substituent, an alkynyl group optionally having a substituent, or an aryl group optionally having a substituent;
and B represents an adenine nucleic acid base optionally protected by one or two acyl groups or an amidine protecting group at the N6 position of the adenine amino group, a cytosine nucleic acid base, a guanine nucleic acid base optionally protected by one or two acyl groups or an amidine protecting group at the N2 position of the guanine amino group, a uracil nucleic acid base optionally protected by an alkyl group or an acyl group at the N3 position, a thymine nucleic acid base optionally protected by an alkyl group or an acyl group at the N3 position, or a pyrimidine base having an alkyl group, an alkynyl group, an aryl group, a fluorescent functional group, a biotinyl group, an amino group or a spin label at the 5-position, or a ribonucleoside derivative represented by General Formula (II):

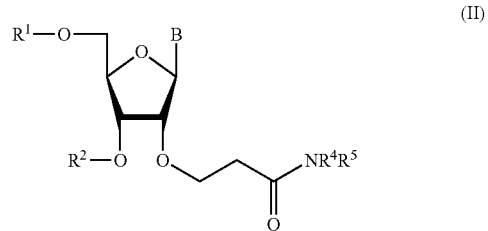

(II)

wherein $R^1$ represents a hydrogen atom or a protecting group for a hydroxyl group;
$R^2$ represents a hydrogen atom, a protecting group for a hydroxyl group, or a group expressed by General Formula (III);
B represents an adenine nucleic acid base optionally protected by one or two acyl groups or an amidine protecting group at the N6 position of the adenine amino group, a cytosine nucleic acid base, a guanine nucleic acid base optionally protected by one or two acyl groups or an amidine protecting group at the N2 position of the guanine amino group, a uracil nucleic acid base optionally protected by an alkyl group or an acyl group at the N3 position, a thymine nucleic acid base optionally protected by an alkyl group or an acyl group at the N3 position, or a pyrimidine base having an alkyl group, an alkynyl group, an aryl group, a fluorescent functional group, a biotinyl group, an amino group or a spin label at the 5-position, or a ribonucleoside derivative represented by General Formula (II);

and $R^4$ and $R^5$ are the same or different and each represents an alkyl group optionally having a substituent, an aralkyl group optionally having a substituent, an alkenyl group optionally having a substituent, an alkynyl group optionally having a substituent, or an aryl group optionally having a substituent, or a nucleic acid derivative containing such a ribonucleoside derivative as a constituent with a reagent containing a fluoride ion to obtain the corresponding ribonucleoside derivative represented by General Formula (IV):

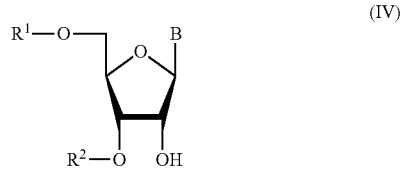

(IV)

wherein $R^1$ represents a hydrogen atom or a protecting group for a hydroxyl group;

$R^2$ represents a hydrogen atom, a protecting group for a hydroxyl group, or a group expressed by General Formula (III);

B represents an adenine nucleic acid base optionally protected by one or two acyl groups or an amidine protecting group at the N6 position of the adenine amino group, a cytosine nucleic acid base, a guanine nucleic acid base optionally protected by one or two acyl groups or an amidine protecting group at the N2 position of the guanine amino group, a uracil nucleic acid base optionally protected by an alkyl group or an acyl group at the N3 position, a thymine nucleic acid base optionally protected by an alkyl group or an acyl group at the N3 position, or a pyrimidine base having an alkyl group, an alkynyl group, an aryl group, a fluorescent functional group, a biotinyl group, an amino group or a spin label at the 5-position, or a ribonucleoside derivative represented by General Formula (II); or a nucleic acid derivative containing the ribonucleoside derivative as a constituent.

* * * * *